US012667729B2

(12) United States Patent
Weiss

(10) Patent No.: US 12,667,729 B2
(45) Date of Patent: Jun. 30, 2026

(54) DEVICE FOR DETECTING A SIGNAL FROM A HUMAN OR ANIMAL ORGANISM

(71) Applicant: BIOTRONIK SE & Co. KG, Berlin (DE)

(72) Inventor: Ingo Weiss, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 453 days.

(21) Appl. No.: 18/247,706

(22) PCT Filed: Oct. 5, 2021

(86) PCT No.: PCT/EP2021/077365
§ 371 (c)(1),
(2) Date: Apr. 3, 2023

(87) PCT Pub. No.: WO2022/073963
PCT Pub. Date: Apr. 14, 2022

(65) Prior Publication Data
US 2023/0405334 A1     Dec. 21, 2023

(30) Foreign Application Priority Data
Oct. 8, 2020    (EP) .................................... 20200789

(51) Int. Cl.
A61N 1/365          (2006.01)

(52) U.S. Cl.
CPC ................................ A61N 1/36514 (2013.01)

(58) Field of Classification Search
CPC .............................. A61N 1/36514; A61B 5/363
See application file for complete search history.

(56) References Cited

U.S. PATENT DOCUMENTS

2013/0226019 A1*   8/2013   Pretorius .................. A61B 5/02
                                                    600/528
2018/0303368 A1    10/2018   Zhang et al.

FOREIGN PATENT DOCUMENTS

CN          108523877 B      2/2021
CN          108685561 B      7/2021
                (Continued)

OTHER PUBLICATIONS

Ganeshapillai et al., "Real time reconstruction of quasiperiodic multi parameter physiological signals", EURASIP Journal on Advances in Signal Processing, 2012, 15 pages, vol. 2012, Article No. 173.
(Continued)

*Primary Examiner* — William J Levicky
(74) *Attorney, Agent, or Firm* — Buchanan Ingersoll & Rooney PC

(57)          ABSTRACT

The invention relates to a device for detecting a signal from a human or animal organism which, during operation, carries out the following steps: detecting a signal from a human or animal organism in a time-dependent manner; subdividing a signal segment into first blocks; determining a total number of the first blocks; determining a measure for a signal swing in each of the first blocks; determining a number of first blocks in which the measure for the signal swing is less than a predeterminable first threshold value; calculating a first quotient from the number of first blocks in which the measure for the signal swing is less than the first threshold value and the total number of first blocks; comparing the first quotient with a second threshold value; classifying a state of the human or animal organism as physiological or as pathophysiological as a function of the previous comparison.

12 Claims, 6 Drawing Sheets

(56) References Cited

FOREIGN PATENT DOCUMENTS

| EP | 2448632 | B1 | 11/2016 |
| JP | 1974104486 | | 10/1974 |
| JP | 2011143060 | A | 7/2011 |
| JP | 2020511216 | A | 4/2020 |
| WO | 2012025815 | A1 | 3/2012 |
| WO | 2020049514 | A1 | 3/2020 |

OTHER PUBLICATIONS

International Search Report (PCT/ISA/210) and Written Opinion (PCT/ISA/237) mailed on Jan. 24, 2022, by the European Patent Office as the International Searching Authority for International Application No. PCT/EP2021/077365. 13 pages.
Japanese Patent Application No. 2023-517847 dated Jul. 10, 2025 (Translation Only).

* cited by examiner

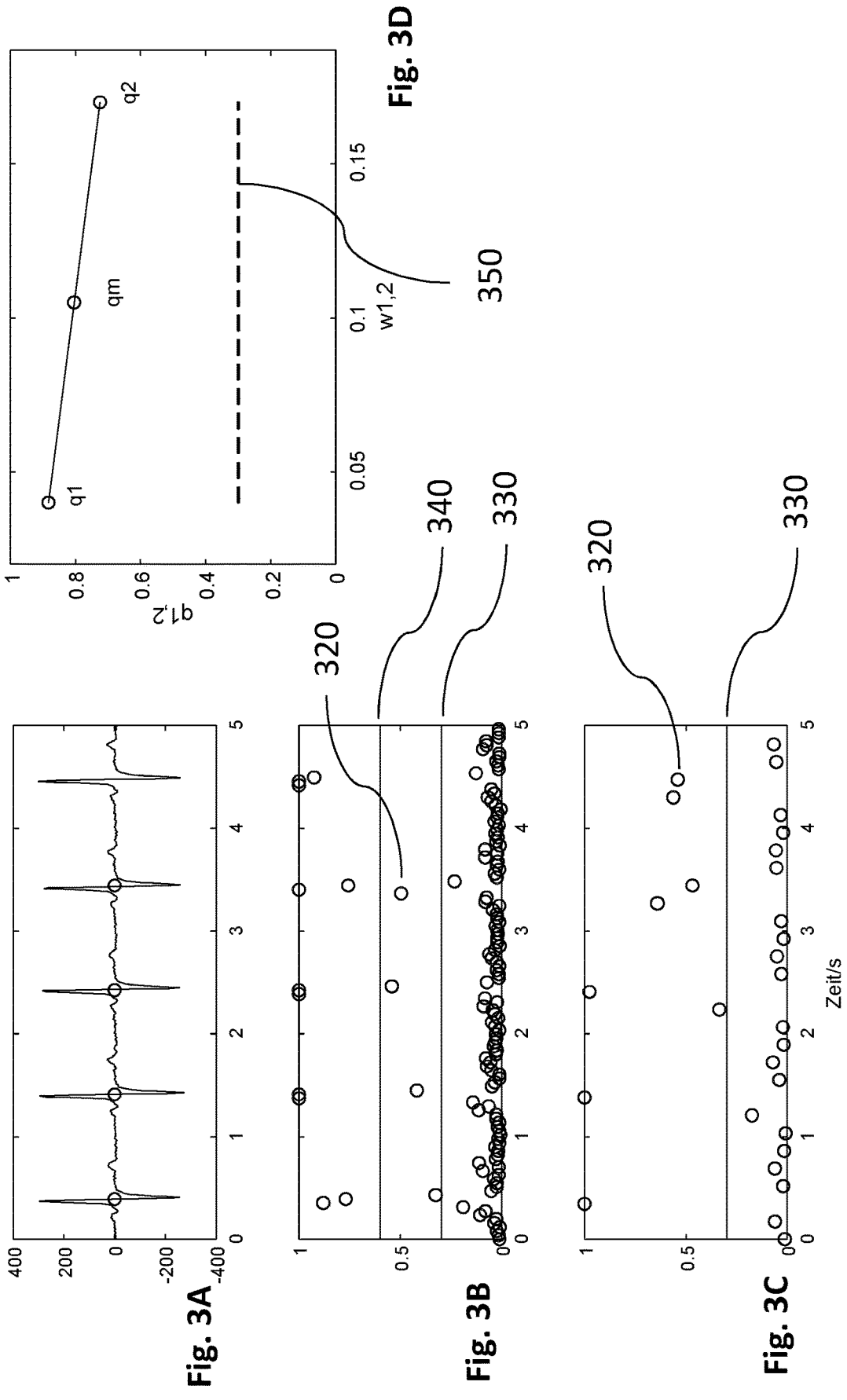

DEVICE FOR DETECTING A SIGNAL FROM A HUMAN OR ANIMAL ORGANISM

CROSS-REFERENCE TO RELATED APPLICATIONS

This application is the United States National Phase under 35 U.S.C. § 371 of PCT International Patent Application No. PCT/EP2021/077365, filed on Oct. 5, 2021, which claims the benefit of European Patent Application No. 20200789.4, filed on Oct. 8, 2020, the disclosures of which are hereby incorporated by reference herein in their entireties.

TECHNICAL FIELD

The present invention relates to a device for detecting a signal from a human or animal organism, a computer program product, and a method for signal processing.

BACKGROUND

Known solutions for evaluating quasi-periodic signals such as electrical signals of the cardiac activity of an organism are predominantly based on event segmentation to be performed in advance. This means that certain events must first be extracted from the measured signal in order to then be able to perform an event-based evaluation of the quasi-periodic signal. This means additional computational effort, which is associated with additional power consumption. In addition, event segmentation is often prone to failure.

In the case of numerous detection devices, particularly in the case of implantable devices, low power consumption is crucial in ensuring a long service life for the devices. Computationally expensive signal processing steps should therefore be avoided in principle.

Known block-based signal evaluation methods mostly also use computationally intensive signal transformations. Such methods are therefore hardly suitable for power-saving detection devices.

Other known signal evaluation methods use heuristic approaches and/or first require training with the aid of training data in order to differentiate between different states. The robustness of the following distinction between process data therefore depends directly on the quality of the training data used previously.

European Patent No. EP 2 448 632 B1 describes a system having means for receiving a heart sound signal from a heart sound sensor, means for detecting a number of heart sounds within the heart sound signal and means for classifying each of the detected heart sounds as either a first classification or a second classification based on one or more characteristics of the detected heart sounds.

U.S. Publication No. 2018/0303368 A1 describes an implantable cardioverter defibrillator (ICD) that performs a method in which, among other things, it is determined whether the first criteria for the recognition of a ventricular tachyarrhythmia are met by an electrical heart signal. For this purpose, the ICD determines features from a cardiac signal segment and determines whether a first part of the features meets monomorphic waveform criteria and whether a second part of the features meets supraventricular beat criteria.

International Publication No. WO 2020/049514 A1 describes a method for selecting stimulation treatment parameter values which comprises the following steps: detecting signals relating to a patient's state during and/or after a brain stimulation session in which a stimulation is delivered to at least one location in the brain; analyzing the detected signals to quantitatively assess a treatment side effect and a symptomatic effect; selecting a set of treatment parameter values based on the quantitative assessment of treatment side effects and symptomatic effect.

The present disclosure is directed toward overcoming one or more of the above-mentioned problems, though not necessarily limited to embodiments that do.

SUMMARY

The present invention is based on the object of providing a simpler and more power-saving option, compared to the known methods, that is able to differentiate between physiological and pathophysiological states of an organism by means of signal analysis.

At least this object is achieved using a device for detecting a signal from a human or animal organism having the features of claim 1.

Such a device has a processor, a storage unit and a detection unit. The detection unit is used to detect a signal from a human or animal organism.

According to the present invention, it is provided that the storage unit has a computer-readable program which causes the processor to carry out the steps explained below when it is executed on the processor.

First, a signal from a human or animal organism is detected as a function of time. This signal can be, for example, a quasi-periodic signal such as a cardiac signal. A signal segment is then defined. This signal segment extends over an adjustable first temporal length of the signal. The signal segment can therefore extend over a smaller or larger time range of the detected time-dependent signal.

In one variant, the time range of the signal segment can be in a range from 2 seconds to 12 seconds, preferably from 3 seconds to 8 seconds.

The signal segment is then subdivided into first blocks in at least a first section of the signal segment. The width of these first blocks (that is, the extent of the blocks along the time axis) can be selected as desired. All blocks of the first section of the signal segment have the same width. The total number of the first blocks is then determined.

A measure for a signal swing in each of the first blocks is then determined. The signal swing characterizes a difference between a minimum signal deflection (that is, a minimum signal value) and a maximum signal deflection (that is, a maximum signal value) within the corresponding block.

The number of first blocks in which the measure for the signal swing is smaller than a predeterminable first threshold value is now determined. As a result, the blocks in which there is only a small or no signal deflection are distinguished from the blocks in which there is a greater signal deflection.

In one variant, the first threshold value can be in a range from 0.15 to 0.7, preferably from 0.2 to 0.6 with respect of the normalized signal in the signal segment.

A quotient is now formed from the number of first blocks in which the measure for the signal swing is smaller than the first threshold value and the total number of the first blocks. The proportion of blocks in which the signal shows only a small amount of deflection is calculated in relation to the total number of blocks. This quotient is now used as a measure of whether the detected and analyzed signal is indicative (representative) of a physiological or a pathophysiological state of the organism. The first quotient is compared with a second threshold value for this purpose. If the first quotient is greater than the second threshold value, a state of the human or animal organism is classified into a first class. If, on the other hand, the first quotient is smaller than the second threshold value or if it corresponds to the second threshold value, the state of the human or animal organism is classified into a second class.

The first or the second class is indicative of a physiological state of the organism. The respective other of the first and second class is indicative of a pathophysiological state of the organism. Which class indicates a physiological state of the organism and which class indicates a pathophysiological state of the organism depends on the detected and analyzed signal.

If, for example, a cardiac electrical signal is detected and evaluated, a sinus rhythm would produce a few blocks having a large signal swing and a larger number of blocks having no or only a small signal swing. The blocks in which a larger signal swing is detected would reflect the individual cardiac contractions. In contrast, the blocks in which only a low signal swing was detected would reflect quiet sections of the cardiac signal that are caused by a heart muscle that is not in motion. Consequently, the first quotient would be large, since the relative proportion of first blocks in which the first threshold value is not exceeded would be small in relation to the total number of first blocks. The first quotient would therefore exceed a suitably selected second threshold value, so that the state of the organism would be classified into the first class. The first class would therefore be indicative of a physiological state of the organism.

In contrast, a tachycardiac state of the organism would lead to the detection of numerous first blocks in which the first threshold value is exceeded. In return, there would only be a few first blocks in which the first threshold value would not be exceeded. Consequently, the first quotient would be low and not exceed a suitably selected second threshold value. The organism would then be classified into the second class. Consequently, the second class would be indicative of a pathophysiological state of the organism, namely a tachycardiac state of the organism.

If, on the other hand, a signal is used in which a quiet signal segment corresponds to a pathophysiological state and a signal segment having a larger signal swing corresponds to a physiological state, the association of the first class and the second class with the corresponding state would be exactly the opposite. Then the first class would indicate a pathophysiological state while the second class would indicate a physiological state.

In one variant, the second threshold value can be in a range from 0.15 to 0.85, preferably from 0.2 to 0.5.

In one variant, the signal segment is additionally subdivided into second blocks in at least a first section of the signal segment. The width of these second blocks (that is, the extent of the blocks along the time axis) can be selected as desired. All second blocks of the first section of the signal segment have the same width. The width of the first blocks differs from the width of the second blocks. The total number of the second blocks is then determined. A measure for a signal swing in each of the second blocks is then determined. The number of second blocks in which the measure for the signal swing is smaller than a predeterminable third threshold value is now determined. As a result, the blocks in which there is only a small or no signal deflection are distinguished from the blocks in which there is a greater signal deflection. A quotient is now formed from the number of second blocks in which the measure for the signal swing is smaller than the third threshold value and the total number of the second blocks. The proportion of blocks in which the signal shows only a small amount of deflection is calculated in relation to the total number of blocks. This second quotient is now used as a further measure of whether the detected and analyzed signal is indicative (representative) of a physiological or a pathophysiological state of the organism. For this purpose, a mathematical combination between the first quotient and the second quotient is compared with a second threshold value. If this mathematical combination between the first quotient and the second quotient is greater than the second threshold value, a state of the human or animal organism is classified into a first class. If, on the other hand, this mathematical combination between the first quotient and the second quotient is smaller than the second threshold value or if it corresponds to the second threshold value, the state of the human or animal organism is classified into a second class. The first threshold value and the second threshold value can be identical for the calculation of the first quotient and the second quotient. The first quotient and the second quotient can be mathematically combined by: a mean value formation, extreme value determination, summation and/or multiplication.

In one variant, the width of the first blocks can be in a range from 0.005 seconds to 0.1 seconds, preferably from 0.02 seconds to 0.08 seconds, more preferably from 0.03 seconds to 0.06 seconds, and even more preferably from 0.035 seconds to 0.05 seconds, and the width of the second blocks in a range from 0.05 seconds to 0.5 seconds, preferably from 0.08 seconds to 0.32 seconds, more preferably from 0.12 seconds to 0.24 seconds, and even more preferably from 0.14 seconds to 0.2 seconds.

In one variant, the above-described can be transferred to sections which, in addition to a subdivision into first blocks and second blocks, have a further subdivision into third blocks.

In one variant, the signal segment is subdivided into blocks in a plurality of sections (that is, in two or more sections). A width of the blocks differs from one another in at least two of these sections. As explained, the width of the blocks corresponds to an extension of the blocks along the time axis of the time-dependent signal. A total number of blocks in each section is then determined in this case. Furthermore, a measure for a signal swing is determined in each of the blocks. A number of blocks in which the measure for the signal swing is smaller than a threshold value that is predeterminable for each section is then determined in each section. Different threshold values can be used in individual sections. It is also possible for the same threshold value to be applied in individual or in all sections. For each section, a quotient is then calculated from the number of blocks in the respective section, in which the measure for the signal swing is smaller than the threshold value, and the total number of blocks in the respective section. This gives an individual quotient for each section. This individual quotient in each section is then compared with a further threshold value. Alternatively, a mathematical combination of the quotients from several (for example, from all) sections of the plurality of sections can also be compared with a further threshold value. The state of the human or animal organism is then classified into the first class if a plurality of the quotients or the mathematical combination of the quotients of several (particularly all) sections is greater than the further threshold value. Alternatively, the state of the human or animal organism is classified into the second class if a majority of the quotients from the individual sections or the mathematical combination of the quotients of several (particularly all) sections is not greater than the further threshold value.

The signal can be analyzed using a different fine grid by subdividing the signal in this way into several sections in blocks of different widths. A very finely rasterized signal analysis is carried out in signal sections in which a subdivision into narrow blocks takes place. A coarser rasterized signal analysis is carried out in signal sections in which the signal is subdivided into wider blocks. Irrespective of whether the signal segment is subdivided into blocks in one or more sections, the signal analysis is based on an analysis of the ratio of the signal swings in individual blocks in relation to the total number of blocks in the corresponding section of the signal segment. As a result, quieter signal sections can be differentiated from noisier signal sections, which ultimately represents the basis for decision-making for the classification of the state of the organism into the first class or the second class.

In one variant, the computer-readable program causes the processor to indicate a measure of the probability that the classification of the state of the organism into the first class and into the second class is actually correct. In this variant, therefore, not only a qualitative classification into the first class or the second class is carried out, but at the same time, a quantitative measure is given for the probability of the correctness of the assignment made.

If the quotient is close to the second or further threshold value, for example, the probability that the assignment to the selected class is correct is lower than in the case where the quotient is a large distance from the second or further threshold value. The quality of the classification carried out can be indicated or checked with this additional quantitative information.

In one variant, the computer-readable program causes the processor to initiate or prevent therapy depending on the classification that has taken place. Such a therapy is typically performed by means of a therapy unit of the device and can consist, for example, in the delivery of an electrical impulse. However, certain chemical or pharmaceutically active substances could also be released from the device in order to achieve a corresponding therapy or therapeutic treatment.

In one variant, the program does not immediately cause the processor to initiate or prevent the therapeutic treatment, but rather makes a corresponding recommendation, which then has to be confirmed by a user, particularly a medically trained user, of the device before the therapy is actually delivered.

In one variant, the detection unit has at least one sensor which is used to detect one of the following parameters of the human or animal organism: an electrical body signal (for example, a cardiac signal or a neurological signal), an impedance, a pressure, a heart sound, a respiratory parameter, a position of the organism, a movement of the organism, a temperature such as the body temperature of the organism, blood oxygen saturation within the organism, a pH value, particularly of the blood, of the organism and a biochemical marker. It is therefore possible in principle for the device to have sensors that are equipped in completely different ways.

In one variant, the sensors were sensors that galvanically record electrical body signals.

In one variant, the sensors are sensors that detect body signals inductively and/or magnetically.

In one variant, the sensors are sensors that determine an impedance. A cardiac state of the organism can be determined, for example, by means of such an impedance measurement. Stress states of the organism can also be determined in this way without detecting the body's own electrical signals. An impedance measurement can be implemented, for example, using subcutaneously implanted sensors. Using such sensors, it is possible to determine a cardiac impedance of the organism without the sensors being in direct contact with the heart of the organism.

In one variant, the signal is subjected to filtering, digitization and/or undersampling during or after the detection. This allows artifacts to be suppressed, whereby an overall better signal quality can be achieved, which ultimately results in a higher accuracy of the classification of the state of the organism to be carried out.

In one variant, the mathematical combination of quotients of several sections comprises averaging, extreme value determination, summation, multiplication and/or quotient formation. In one variant, the measure for the signal swing and/or one or more quotients can be used to form a threshold. For example, it is possible to adaptively adapt the first threshold value, the second threshold value and/or a further threshold value to the measurement results obtained in the course of the method in order to enable patient-specific signal evaluation.

In one variant, the device has one or more ring buffers for the temporary storage of measured values or intermediate results obtained. Such a ring buffer can be designed as part of the storage unit or, taken by itself, form a separate storage unit.

In one variant, a length of the first section of the signal segment and/or of a further section of the signal segment is adapted as a function of a result that was determined in a previous step of the method performed. This variant therefore enables the length of the signal segments to be adapted adaptively as a function of previously determined results or intermediate results. For example, it is possible for the length of a further section to be adapted as a function of a result that was achieved for the previous section. In the same way, it is possible in one variant for the width of the blocks to be adaptively adapted during the method as a function of a previously obtained result or intermediate result, particularly as a function of a result in relation to the previous section.

In one variant, the total number of blocks per section is selected such that the total number corresponds to a power of two (for example, 2, 4, 8, 16, 32, 64, 128, 256, 512, 1024).

In one variant, the ratio of the width of the first blocks and the width of the further blocks in a further section is an integer. It has been found that a finer gradation of the width of the blocks does not lead to a significant improvement in the accuracy of the classification of the state of the organism.

In one variant, the ratio of the width of the first blocks in the first section and the further blocks in a further section is a power of two (for example, 2, 4, 8, 16, 32, 64, 128, 256, 512, 1024). This enables a sufficiently fine gradation of the width of the blocks used for the segmentation to be achieved.

In one variant, the measure for the signal swing is a maximum-minimum difference, a signal variance or a percentile interval. When forming a maximum-minimum difference, the entire signal swing is taken into account as a measure for the signal swing. That is because this then forms the difference between the smallest signal value in the corresponding block and the largest signal value in the corresponding block. When using a percentile interval, it is possible to use only part of the signal swing as a measure for the signal swing. In this way, particularly meaningful signal swing sections can be used as a measure for the signal swing. Suitable percentile intervals are, for example, a 99th percentile, particularly a 98th percentile, particularly a 97th percentile, particularly a 96th percentile, particularly a 95th percentile, particularly a 90th percentile, particularly an 85th percentile, particularly an 80th percentile.

In one variant, quotients of at least two sections are used to classify the state of the organism into the first class or the second class. The individual values of the quotients of the respective sections then span a multi-dimensional decision space. In this multi-dimensional decision space, suitable additional discrimination features can be used in order to be able to provide for a differentiation between the individual quotients which is necessary for the desired classification. For example, in one variant, it is possible for the states in the multidimensional decision space to be delimited from one another by surfaces such as hypersurfaces. Thus, such surfaces act as dividing surfaces between quotients or values of quotients that are representative of a first state that is to be classified into the first class, and quotients or values of quotients that are representative of a second state that is to be classified into the second class.

In one variant, the aforementioned separating surfaces can be described as an implicit function of i values of a quotient q. This function can be, for example, $F(qj)=0$, wherein qj is the total or a subset of all qi. qj is to be understood as a vector here. In the case of a one-dimensional result space, this function is a simple one-dimensional threshold value consideration. In the two-dimensional case, however, a curve for separating different states is used as the threshold value.

In one variant, the separating surfaces are designed as planes or as surfaces of the second or higher order. In a further variant, the separating surfaces are designed as surfaces that are described by a combination of mathematical elementary functions. In a further variant, the separating surfaces are designed as surfaces that are described and put together in regions. In a further variant, the separating surfaces are designed as surfaces that are described by triangulation or a comparable approximation method. In all these ways, it is possible to create very specific dividing surfaces between values that are to be associated with the first class and values that are to be associated with the second class. Application-specific value classifications that take signal-specific characteristics into account can be made in this way.

In one variant, in addition to the first quotient, a further variable is used to classify the state of the human or animal organism into the first class or the second class. As a result, the dimension of the decision space is expanded, which in turn enables a more refined separation of the first class from the second class, so that a more precise state classification is achieved. It is possible to use the further variable as a functional argument for the separating surfaces used for separation.

In one variant, the further or additional variable is a heart rate, a blood pressure, a breathing frequency and/or a breathing depth of the human or animal organism. Together with the detected signal, these variables then provide additional physiological information about the organism so that its state can be classified even more precisely as physiological or pathophysiological.

In one variant, the signal segment is subdivided into blocks in a plurality of sections of the signal segment. In this case, at least two sections of the plurality of sections at least partially overlap one another. This means that blocks that are associated with both a first section and a second section are evaluated twice in this variant. If the corresponding blocks have different widths, the signal contained in the blocks of the overlapping sections is analyzed on the one hand with a finer, and, on the other hand, with a coarser grid. This can provide additional information, which in turn results in a more precise classification of the state of the organism.

In one variant, the device is provided and set up for cardiological applications. In other words, the device in one variant is an implantable device for stimulating the human or animal heart. Examples of such implantable devices are implantable pulse generators (IPGs), implantable cardioverter-defibrillators (ICDs), and cardiac resynchronization therapy devices (CRT-D). Such devices typically detect the body's own cardiac electrical signals, which are then fed to the evaluation described here. Furthermore, it is possible in a variant of such devices to determine a body impedance or cardiac impedance by means of an applied voltage in order to then feed this impedance as a signal to the evaluation described here.

In one variant, the device is used to detect a subcutaneous electrocardiogram. By determining the proportion of flat signal sections, it is determined how long the examined heart has been in an electrically stationary state, that is, is either tense (systole) or slack (diastole). The corresponding proportion is also referred to as the so-called steady state ratio (SSR).

Sufficient hemodynamics can only be ensured if the heart is in such a temporarily stationary state for a sufficiently long period of time. The result of the classification of the state of the organism therefore allows an immediate physiological interpretation which is far superior to the widely used, empirically developed and/or trained methods known from the prior art. Concrete physiological information about the hemodynamic state is also of great importance when deciding for or against performing shock therapy. Inadequate shocks can consequently be avoided better than has hitherto been possible when using a device described here.

It is not necessary to identify individual heartbeats for the method that is performed by the presently claimed device. Rather, a signal evaluation can take place without such identification of individual heartbeats; so no event-based signal evaluation is required. Rather, the corresponding signal evaluation distinguishes between physiological cardiac states such as a sinus rhythm of the heart or non-tachycardic states of the heart from pathophysiological cardiac states such as tachycardiac states. This makes it possible to make statements about the hemodynamic state of the organism on the basis of this signal evaluation. This is because the signal evaluation makes it immediately clear whether the heart of the organism being examined has sufficient pumping capacity. If no phases of a quieter heartbeat are detected during the evaluation, this indicates an enduring tachycardic state of the heart, which in turn is synonymous with insufficient pumping capacity of the heart. A pathological hemodynamic state of the organism can consequently be recognized in this way, even if a heart rate of the organism is not determined separately at all.

In one variant, however, the device has at least one heart rate estimator with which the heart rate (that is, the frequency of the heartbeat) of the organism can also be determined. With the additional information on the heart rate, malignant and non-malignant heart rhythms of the organism can be distinguished particularly well.

In one variant, the pathophysiological state of the organism comprises a ventricular tachycardia or a supraventricular tachycardia. In principle, it is also possible to make a differential diagnosis between such tachycardiac states and ventricular fibrillation.

If the device is designed as an implantable cardioverter defibrillator (ICD), the classification of the state of the organism into the first class or the second class is used in a variant to support the decision of the ICD to deliver shock therapy as a therapeutic treatment of the organism or to prevent the delivery of such shock therapy. Therapy can also be delivered when the heart rate is not particularly high at all, but the signal of the heartbeat has few quiet sections. This is because that this is, as explained above, an indication of insufficient pumping capacity of the heart, which indicates a critical hemodynamic state of the organism.

Such a shock delivery is typically delivered by a stimulation unit of the device. Such a stimulation unit can also be used for other stimulations of a cardiac area of the heart of the organism. In principle, it is thus possible, depending on the classification that has taken place, to initiate or prevent stimulation of a cardiac area by means of the stimulation unit. In this case, the stimulation is consequently to be regarded as therapy or therapeutic treatment. Its purpose is to end a pathophysiological state of the heart or to reduce the effects of a pathophysiological state on the overall state of the organism.

In one variant, the device has more than one heart rate estimator, wherein the selection of the heart rate estimator used for estimating the heart rate takes place as a function of the first quotient and/or the further quotients. The individual heart rate estimators typically use different algorithms to estimate the heart rate. When evaluating the signal, a plausibility check can then be carried out on whether the determined values appear plausible (regardless of the specific state of health of the organism). If this is not the case, another heart rate estimator can be used in order to obtain basically plausible results, which are then evaluated according to the signal evaluation method described here.

In one variant, the device has a remote data transmission unit which is provided and set up to communicate with a remotely located server. A remote monitoring system, a so-called home monitoring system, for example, can be implemented on such a server. It is then possible to monitor and control the device remotely and thus to obtain information about the state of health of the organism, even if it is not being examined directly by a physician. It is further possible in this way to remotely make or confirm the decision to deliver therapy, such as shock therapy, for example.

In one variant, the device is provided and set up to communicate with a medical device, particularly an implantable medical device. This can be done, for example, via a direct data exchange. It is further possible for such a data exchange to take place via a server or a data communication device. For example, it is possible that both the device is equipped as an implantable medical device and the medical device is configured as an implant.

Communication between the two implants can then take place directly or by means of a data communication unit arranged outside the body of the organism. The medical device can, for example, be able to measure or estimate a heart rate of the organism.

In one embodiment, the device is equipped as an implantable device which does not impair a magnetic resonance examination (MRI) of a patient in whom the device was implanted and which is not itself impaired by such a magnetic resonance examination. In other words, the device in this embodiment is designed as an MRI-compatible implant.

One aspect of the present invention relates to a computer program product having a computer-readable code which causes a processor to carry out the steps explained below when it is executed on the processor.

First, a signal from a human or animal organism is detected as a function of time by means of a detection unit of a device for detecting a signal from a human or animal organism. A signal segment is then defined. This signal segment extends over an adjustable first temporal length of the signal. The signal segment can therefore extend over a smaller or larger time range of the detected time-dependent signal.

The signal segment is then subdivided into first blocks in at least a first section of the signal segment. The width of these first blocks (that is, the extent of the blocks along the time axis) can be selected as desired. All blocks of the first section of the signal segment have the same width. The total number of the first blocks is also determined.

A measure for a signal swing in each of the first blocks is then determined. The signal swing characterizes a difference between a minimum signal deflection (that is, a minimum signal value) and a maximum signal deflection (that is, a maximum signal value) within the corresponding block.

The number of first blocks in which the measure for the signal swing is smaller than a predeterminable first threshold value is now determined. As a result, the blocks in which there is only a small or no signal deflection are distinguished from the blocks in which there is a greater signal deflection.

A quotient is now formed from the number of first blocks, in which the measure for the signal swing is smaller than the first threshold value, and the total number of the first blocks.

The proportion of blocks in which the signal shows only a small amount of deflection is calculated in relation to the total number of blocks. This quotient is now used as a measure of whether the detected and analyzed signal is indicative (representative) of a physiological or a pathophysiological state of the organism. The first quotient is compared with a second threshold value for this purpose. If the first quotient is greater than the second threshold value, a state of the human or animal organism is classified into a first class. If, on the other hand, the first quotient is smaller than the second threshold value or if it corresponds to the second threshold value, the state of the human or animal organism is classified into a second class.

The first or the second class is indicative of a physiological state of the organism. The respective other of the first and second class is indicative of a pathophysiological state of the organism.

One aspect of the present invention relates to a method for signal processing comprising the steps explained below.

First, a signal from a human or animal organism is detected as a function of time by means of a detection unit of a device for detecting a signal from a human or animal organism. A signal segment is then defined. This signal segment extends over an adjustable first temporal length of the signal. The signal segment can therefore extend over a smaller or larger time range of the detected time-dependent signal.

The signal segment is then subdivided into first blocks in at least a first section of the signal segment. The width of these first blocks (that is, the extent of the blocks along the time axis) can be selected as desired. All blocks of the first section of the signal segment have the same width. The total number of the first blocks is also determined.

A measure for a signal swing in each of the first blocks is then determined. The signal swing characterizes a difference between a minimum signal deflection (that is, a minimum signal value) and a maximum signal deflection (that is, a maximum signal value) within the corresponding block.

The number of first blocks in which the measure for the signal swing is smaller than a predeterminable first threshold value is now determined. As a result, the blocks in which there is only a small or no signal deflection are distinguished from the blocks in which there is a greater signal deflection.

A quotient is now formed from the number of first blocks in which the measure for the signal swing is smaller than the first threshold value and the total number of the first blocks. The proportion of blocks in which the signal shows only a small amount of deflection is calculated in relation to the total number of blocks. This quotient is now used as a measure of whether the detected and analyzed signal is indicative (representative) of a physiological or a patho-physiological state of the organism. The first quotient is compared with a second threshold value for this purpose. If the first quotient is greater than the second threshold value, a state of the human or animal organism is classified into a first class. If, on the other hand, the first quotient is smaller than the second threshold value or if it corresponds to the second threshold value, the state of the human or animal organism is classified into a second class.

The first or the second class is indicative of a physiological state of the organism. The respective other of the first and second class is indicative of a pathophysiological state of the organism.

Based on the performed comparison between the first quotient and the second threshold value, the method for signal processing then enables a later classification of a state of the human or animal organism. This classification allows a classification into a first class and into a second class. The first class is selected when the first quotient is greater than the second threshold value. The second class is selected if the first quotient is not greater than the second threshold value. One of the first and second classes is indicative of a physiological state of the organism. The other of the first and second class is indicative of a pathophysiological state of the organism. The method for signal processing thus supplies output data, on the basis of which analytical and/or diag-nostic results can then be achieved with regard to the state, particularly the state of health, of the organism.

One aspect of the present invention relates to a medical method for classifying a state of a human or animal organ-ism as physiological or as pathophysiological. Such a medi-cal method comprises all of the aforementioned steps of the method for signal processing and a subsequent classification step.

In this classification step, the first quotient is compared with a second threshold value. If the first quotient is greater than the second threshold value, a state of the human or animal organism is classified into a first class. If, on the other hand, the first quotient is smaller than the second threshold value or if it corresponds to the second threshold value, the state of the human or animal organism is classified into a second class. The first or the second class is indicative of a physiological state of the organism. The respective other of the first and second class is indicative of a pathophysiologi-cal state of the organism.

The medical method thus provides direct analytical or diagnostic findings on the state of health of the organism. In one variant, the method also comprises a therapeutic step for the therapeutic treatment of a determined pathophysiologi-cal state. For this purpose, the method is expanded to include a therapy delivery step. In this respect, reference is made to the above explanations on the possible therapy delivery.

All variants and alternative configurations of the device can be combined with one another in any way and can be transferred individually or in any combination to the com-puter program product or to one of the methods described. In the same way, all variants and alternative configurations of the computer program product can be combined with one another as desired and transferred individually or in any combination to the device or to one of the methods described. Finally, the variants and alternative configura-tions of the different methods can also be combined with one another as desired and transferred individually or in any combination to the device, the computer program product or one of the other methods.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

Further details of aspects of the present invention are explained in more detail below with reference to embodi-ments and drawings. Shown are:

FIG. 3A an illustration of a cardiac electrical signal having a sinus rhythm originating from a heart;

FIG. 3B a first graphic representation of an intermediate result of a signal processing of the signal from FIG. 3A;

FIG. 3C a second graphic representation of an interme-diate result of a signal processing of the signal of FIG. 3A;

FIG. 3D a third graphic representation of an intermediate result of a signal processing of the signal of FIG. 3A;

DETAILED DESCRIPTION

Figure 1:
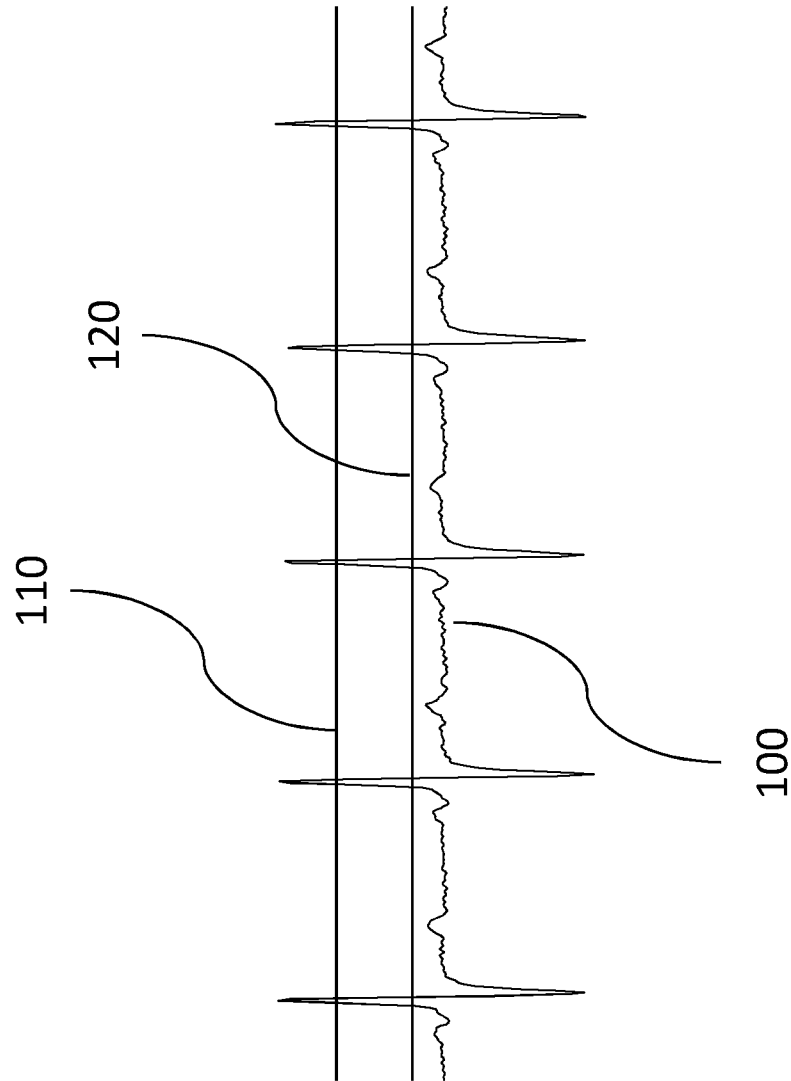
FIG. 1 a schematic representation of a discrete-event signal processing known from the prior art.

FIG. 1 shows an exemplary illustration of a cardiac electrical signal 100 for the visualization of a discrete-event signal processing known from the prior art.

First, individual cardiac cycles are determined in the cardiac signal 100 on the basis of a comparison with a first threshold 110. In addition, it is customary to use a second threshold 120 in order to evaluate statistical features between the first threshold 110 and the second threshold 120. This type of signal processing is based on the actual physi-ological events (individual cardiac contractions) and the subsequent evaluation is based on the detected events.

Figures 2A, 2B:
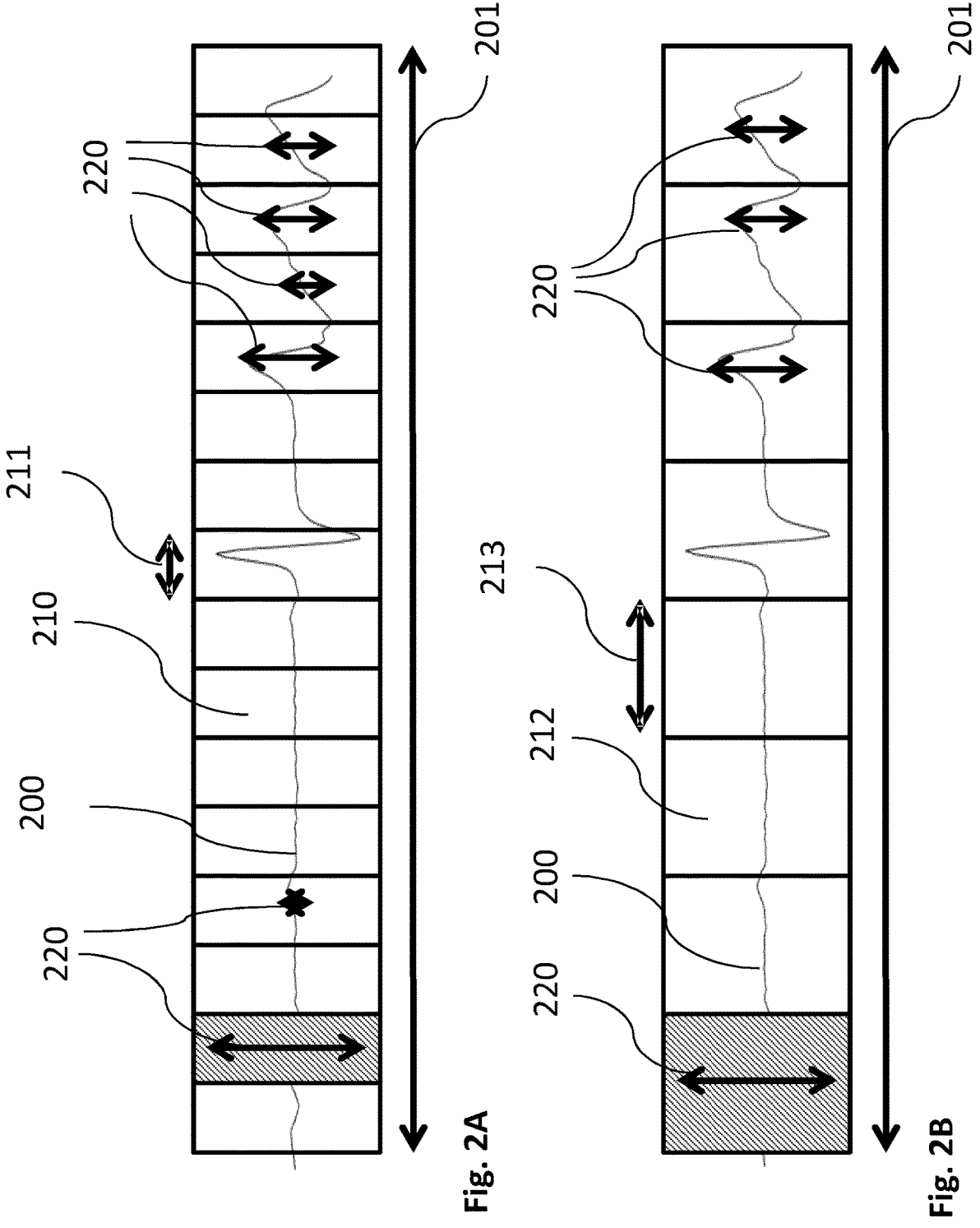
FIG. 2A a section of a signal segment subdivided into blocks of the first width.
FIG. 2B the same section of the signal segment of FIG. 2A, but which is subdivided into blocks of greater width than in FIG. 2A.

FIG. 2A shows a first representation of signal processing in accordance with a method of the present disclosure. First, a cardiac electrical signal 200 is detected as a signal from a human or animal organism. This cardiac electrical signal 200 is a time-dependent signal.

A signal segment 201 which extends over an adjustable length of the cardiac electrical signal 200 is then determined. The signal segment 201 is then subdivided into a plurality of blocks 210, only one of which is provided with the corresponding reference number. These blocks 210 have a first width 211, which extends along the temporal course of the cardiac electrical signal 200.

In each of the blocks 210, a minimum-maximum difference 220 is then formed between the lowest signal value and the highest signal value in the corresponding block 210. This minimum-maximum difference 220 is a measure of the signal swing in the corresponding block 210. No arrows for visualizing the minimum-maximum difference 220 are drawn in blocks 210 in which the signal 200 does not experience any significant deflection. The minimum-maximum differences 220 determined are then compared with a threshold value. This is explained in more detail in FIG. 3.

The same signal segment 201 of the cardiac electrical signal 200 as shown in FIG. 2A is shown in FIG. 2B. In the case of the embodiment shown in FIG. 2B, however, the signal segment 201 is subdivided into fewer blocks 212 which have a greater width 213 than the width 211 of the blocks 210 according to the embodiment in FIG. 2A. Consequently, overall fewer minimum-maximum differences 220 are also determined as a measure of the signal swing of cardiac electrical signal 200, wherein minimum-maximum differences 220 of blocks 212 are not necessarily greater than minimum-maximum differences 220 of blocks 210.

FIG. 3A shows a signal section of a cardiac electrical signal which represents a sinus rhythm of the heart. As shown in FIGS. 2A and 2B, this signal section is subdivided into blocks. The signal swing in each block is then determined from the minimum-maximum difference. The corresponding values of the minimum-maximum difference 320 are shown in FIG. 3B. Only a single value is provided with the corresponding reference number for the sake of clarity. These minimum-maximum differences 320 are now compared with a first threshold value 330. As can be seen from FIG. 3B, some of the minimum-maximum differences 320 lie above the first threshold value 330, while most of the minimum-maximum differences 320 lie below the first threshold value 330.

The method, the evaluation of which is shown in FIGS. 3A to 3D, also uses two heart rate estimators. The first heart rate estimator considers the blocks whose minimum-maximum differences lie above a threshold value 340. This threshold value shall be referred to as the heart rate threshold value 340. Of the minimum-maximum differences 320 which lie above the heart rate threshold value 340, those are sorted out which are closer than an adjustable minimum distance to the previous value of a minimum-maximum difference 320. The time intervals are determined between the remaining, not sorted-out minimum-maximum differences 320. The heart rate of the patient under consideration is approximately calculated from the median of the time intervals per signal segment. The second heart rate estimator counts the zero crossings of the cardiac electrical signal (compare FIG. 3A, in which the zero crossings are marked with circles).

In FIG. 3C, a comparable evaluation of minimum-maximum differences 320 is carried out as in FIG. 3B. However, the minimum-maximum differences in FIG. 3C are based on a subdivision of the cardiac electrical signal into wider blocks than in the case of FIG. 3B. Thus, the blocks used for the results in FIG. 3B have a width of 0.04 seconds, while the blocks for the results in FIG. 3C have a width of 0.17 seconds. This results in overall fewer values for minimum-maximum differences 320 in FIG. 3C than in FIG. 3B. The first threshold value 330 is selected to be the same in the evaluation of the blocks having a larger width (FIG. 3C) as in the case of the evaluation of the blocks having a smaller width (see FIG. 3B).

The number of minimum-maximum differences 320 which lie below threshold value 330 is now divided by the total number of blocks. This results in a first quotient q1 for the evaluation according to FIG. 3B and a second quotient q2 for the evaluation according to FIG. 3C.

These quotients q1 and q2 are now plotted in FIG. 3D over the width of the blocks of the underlying signal analyses. Furthermore, the first quotient q1 and the second quotient q2 are compared with a second threshold value 350. At the same time, a mean value qm of the first quotient q1 and the second quotient q2 is also formed.

As can be seen from FIG. 3D, both the first quotient q1 and the second quotient q2 lie significantly above the second threshold value 350. The state of the examined patient is thus classified into a first class. This first class is indicative of a physiological state of the patient. No further action is therefore required to treat the patient.

Figures 4A, 4B, 4C, 4D:
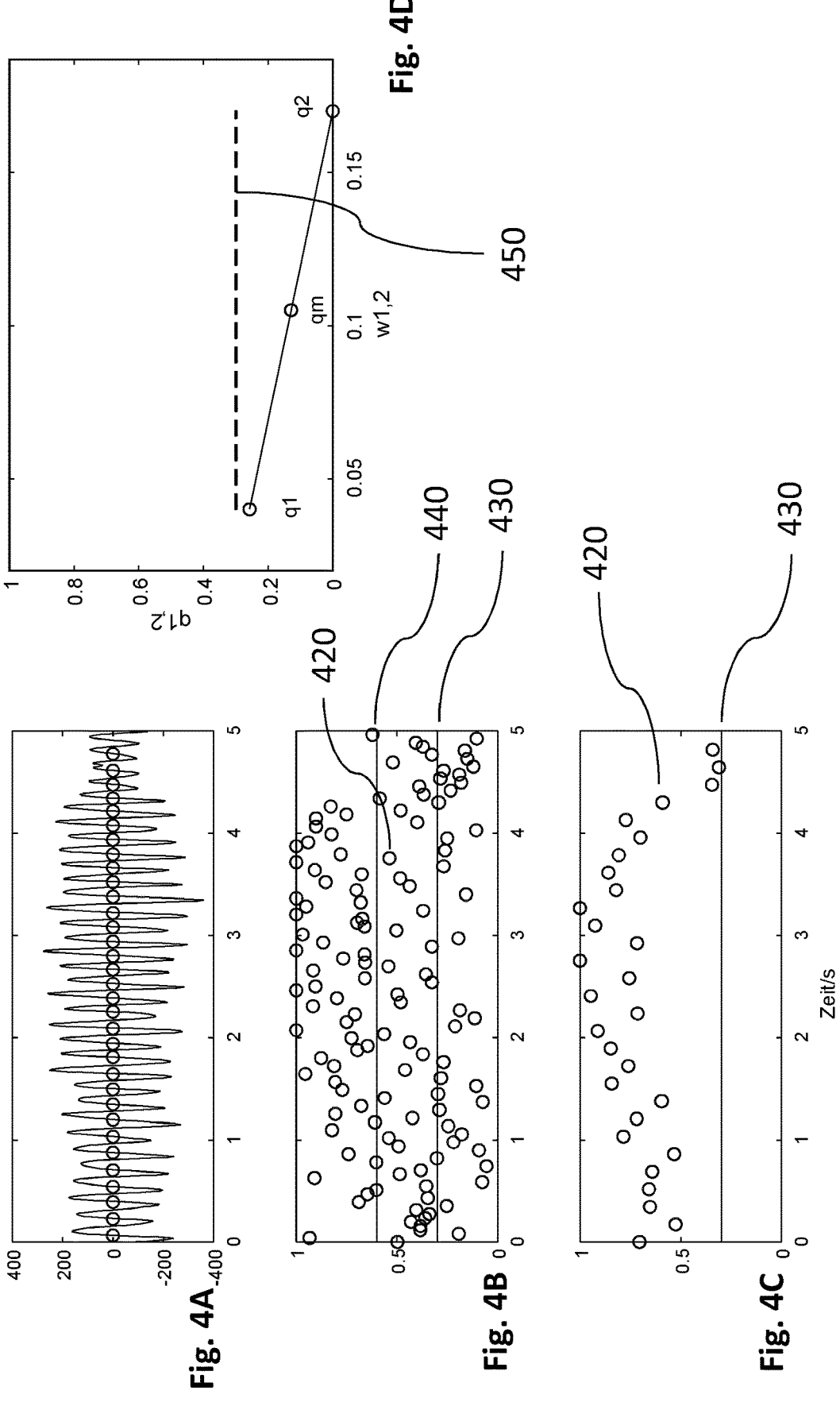
FIG. 4A a representation of a cardiac electrical signal having ventricular fibrillation originating from a heart.
FIG. 4B a first graphic representation of an intermediate result of a signal processing of the signal from FIG. 4A.
FIG. 4C a second graphic representation of an interme-diate result of a signal processing of the signal of FIG. 4A.
FIG. 4D a third graphic representation of an intermediate result of a signal processing of the signal of FIG. 4A.

FIG. 4A shows a representation of an electrical cardiac signal comparable to FIG. 3A. However, no sinus rhythm can be seen here, but rather ventricular fibrillation.

Consequently, there are numerous minimum-maximum differences 420 which lie above the first threshold value 430 (compare to FIG. 4B). If a subdivision of the signal segment into blocks of small width (0.04 seconds) is chosen, some of the minimum-maximum differences 420 will also lie below the first threshold value 430. In contrast, all minimum-maximum differences lie above the first threshold value 430 if blocks having a greater width (0.17 seconds) are selected, as is shown in FIG. 4C.

Since numerous minimum-maximum differences 420 lie above the heart rate threshold value 440 (compare the corresponding explanations for FIG. 3B), a second heart rate estimator is used, which only counts the zero crossings of the electrical cardiac signal in order to estimate the heart rate.

Now the portion of the minimum-maximum differences 420 lying below the first threshold value 430 is determined again and plotted against the width of the blocks used to subdivide the signal segment. This is shown in FIG. 4D. Both the first quotient q1, which results from the evaluation in FIG. 4B, and the second quotient q2, which results from the evaluation in FIG. 4C, lie below the second threshold value 350. Thus, the state of the examined patient is classified into the second class, which is indicative of a pathophysiological state of the patient. The patient's state of health is therefore classified as pathophysiological due to the ventricular fibrillation.

Figure 5:
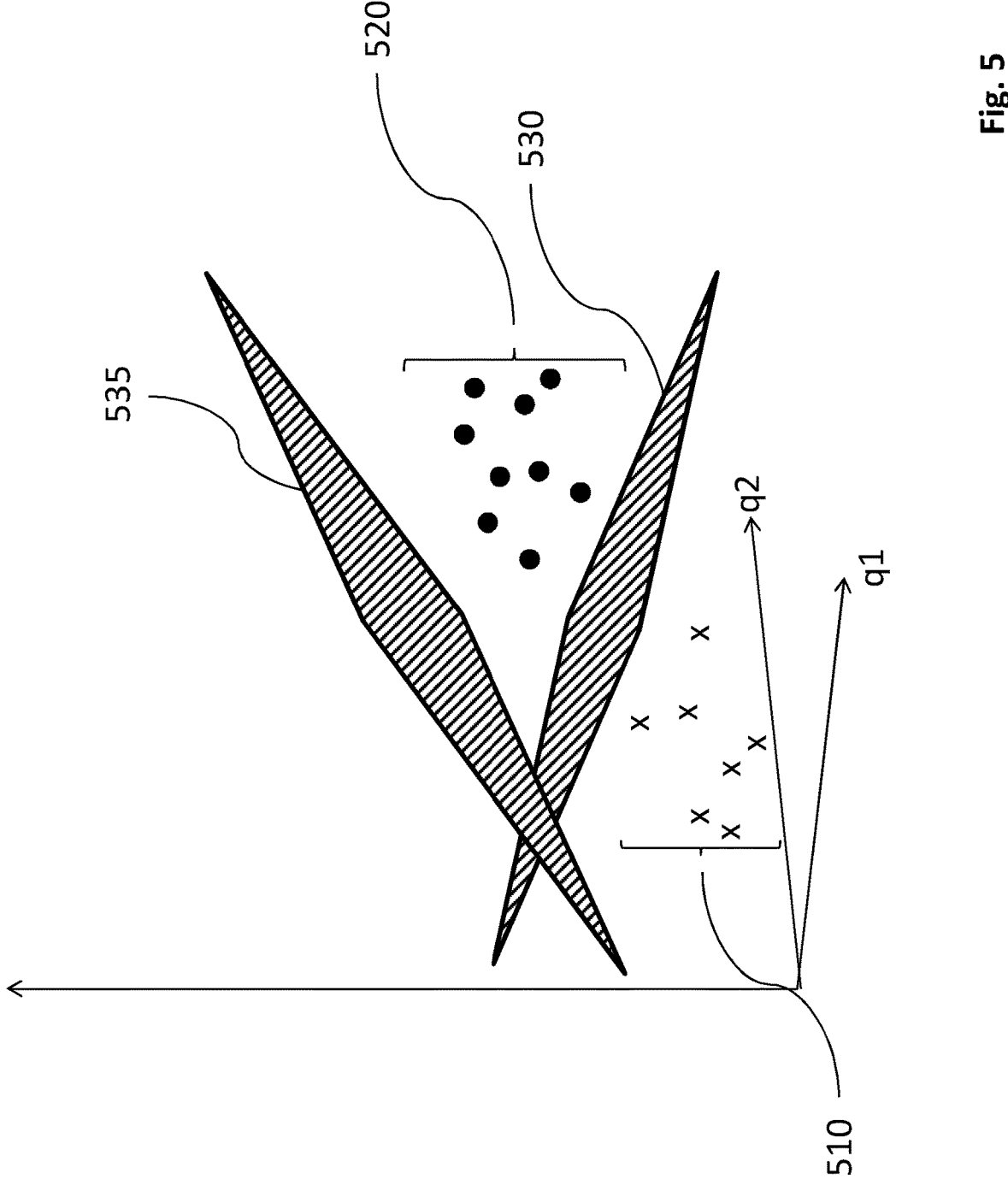
FIG. 5 an exemplary decision space for the classification of values which reflect a first or a second state.

FIG. 5 shows an exemplary illustration of a multidimensional decision space for classifying obtained minimum-maximum differences into a first class and a second class. The decision space is spanned by the first quotient q1, the second quotient q2 and the heart rate HR. The heart rate HR was determined by a heart rate estimator, as explained in connection with FIGS. 3A to 3D and 4A to 4D. In principle, however, it would also be possible to introduce heart rate information from an external source.

In the multidimensional decision space, a first group 510 of quotients is separated from a second group 520 of quotients by means of a separating surface 530. The first group 510 is associated with a first class, which indicates a physiological or non-malignant state of the patient. The second group 520 of quotients is associated with a second class, which indicates a pathophysiological or malignant state of the patient.

It is possible to use further separating surfaces such as the second separating surface 535 for plausibility checks. In the present embodiment, quotients that lie above the second separating surface 535 are unexpected. If a value of a quotient above this second separating surface 535 is nevertheless observed, this indicates that a correction must be made during the signal evaluation. For example, it may be necessary to use a different heart rate estimator to estimate the heart rate. The specific measure to be performed depends on the definition of the further separating surfaces and the associated significance of these separating surfaces for the signal processing method.

Figure 6:
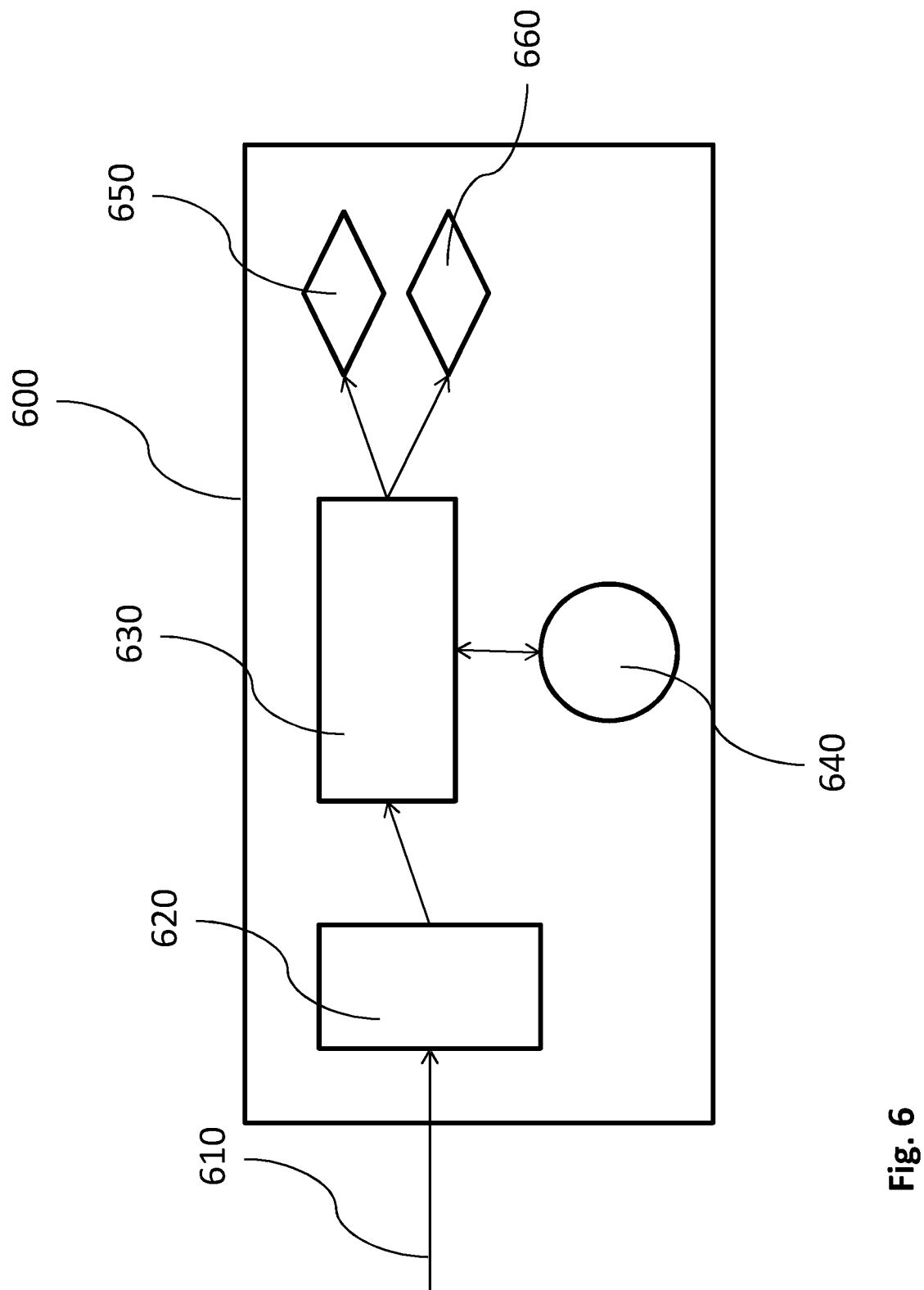
FIG. 6 a block diagram of an exemplary device for detecting a signal from a human or animal organism.

FIG. 6 shows a block diagram of an embodiment of an implant 600 for stimulating the heart. The implant 600 serves as a device for detecting a signal from a human or animal organism. This implant 600 has an energy source (not shown). The implant 600 is used to detect body signals 610. This takes place by means of a detection unit 620 which is equipped with appropriate sensors. The detection unit 620 is connected to a processor 630. This processor 630 can call up and execute program code from a storage unit 640. The processor 630 now executes a method as shown by way of example in FIGS. 2A to 5. This makes it possible to classify a state of the organism from which the body signals 610 originate into a first class 650 (physiological state) or into a second class 660 (pathophysiological state). The corresponding result can then be used for further steps that the processor 630 initiates. For example, in the case of a determined pathophysiological state 660, a stimulation unit (not shown) can be used to electrically stimulate a heart in order to convert a pathophysiological state such as a tachycardiac state into a physiological state such as a non-tachycardiac state.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

The invention claimed is:

1. An implantable medical device for detecting a cardiac signal from a human or animal organism and for stimulating the human or animal heart, having a processor, a storage unit, a stimulation unit and a detection unit for detecting a cardiac signal from a human or animal organism, wherein, the storage unit has a computer-readable program that causes the processor to carry out the following steps when it is executed on the processor:

a) detecting a cardiac signal of a human or animal organism in a time-dependent manner;

b) defining a signal segment which extends over an adjustable first temporal length of the cardiac signal;

c) subdividing the signal segment into first blocks in at least a first section of the signal segment;

d) determining a total number of the first blocks;

e) determining a measure for a signal swing in each of the first blocks;

f) determining a number of first blocks in which the measure for the signal swing is less than a predeterminable first threshold value;

g) calculating a first quotient from the number of first blocks in which the measure for the signal swing is less than the first threshold value, and the total number of the first blocks;

h) comparing the first quotient with a second threshold value;

i) classifying a cardiac state of the human or animal organism into a first class if the first quotient is greater than the second threshold value, or classifying a cardiac state of the human or animal organism into a second class if the first quotient is not greater than the second threshold value, wherein one of the first and second classes is indicative of a physiological state of the organism and the other of the first and second classes is indicative of a pathophysiological state of the organism;

wherein the computer-readable program causes the processor to initiate or prevent a stimulation of a cardiac region of the heart of the human or animal organism by means of the stimulation unit depending on the classification that has taken place.

2. The device according to claim 1, wherein the computer-readable program causes the processor to subdivide the cardiac signal into blocks in a plurality of sections, the plurality of sections including the first section and at least one additional section, wherein a width of the blocks differs from one another in at least two sections of the plurality of sections, wherein a total number of the blocks is determined in each section, wherein a measure of a signal swing in each of the blocks is determined, wherein a number of blocks, in which the measure for the signal swing is less than a threshold value predeterminable for each section, is determined in each section, wherein for each section, a quotient from the number of blocks in the respective section in which the measure for the signal swing is less than the threshold value and the total number of blocks in the respective section is calculated, wherein the quotient in each section is compared with a further threshold value or a mathematical combination of the quotients of several sections is compared with a further threshold value, wherein the cardiac state of the human or animal organism is classified into the first class if a majority of the quotients or the mathematical combination of the quotients of several sections is greater than the further threshold value or the cardiac state of the human or animal organism is classified into the second class if a majority of the quotients or the mathematical combination of the quotients of several sections is not greater than the further threshold value.

3. The device according to claim 1, wherein the computer-readable program causes the processor to indicate a measure for a probability that the classification of the cardiac state of the human or animal organism into the first class or the second class is correct.

4. The device according to claim 1, wherein the detection unit has at least one sensor which is used to detect at least one of the following parameters of the human or animal organism: an electrical body signal, an impedance, a pressure, a heart sound, a respiratory parameter, a position, a movement, a temperature, a blood oxygen saturation, a pH value, a biochemical marker.

5. The device according to claim 1, wherein the computer-readable program causes the processor to adapt a length of the first section of the signal segment and/or a further section of the signal segment as a function of a result determined in a previous step of the method performed.

6. The device according to claim 1, wherein the measure for the signal swing is selected from the group consisting of a maximum-minimum difference, a signal variance and a percentile interval.

7. The device according to claim 1, wherein the computer-readable program causes the processor to use, in addition to the first quotient, a further variable for classifying the state of the human or animal organism into the first class or the second class.

8. Device according to claim 7, wherein the further variable is selected from a heart rate, a blood pressure, a breathing frequency and a breathing depth of the human or animal organism.

9. The device according to claim 1, wherein the computer-readable program causes the processor to subdivide the signal segment into blocks in a plurality of sections of the signal segment, the plurality of sections including the first section and at least one additional section, wherein at least two sections of the plurality of sections overlap one another in regions.

10. The device according to claim 1, wherein the device has at least one heart rate estimator.

11. A storage unit including a computer program product having computer readable code that causes a processor to carry out the following steps when executed on the processor:

a) detecting a cardiac signal from a human or animal organism in a time-dependent manner by means of a detection unit of an implantable medical device for detecting a cardiac signal from a human or animal organism and for stimulating the human or animal heart;

b) defining a signal segment which extends over an adjustable first temporal length of the cardiac signal;

c) subdividing the signal segment into first blocks in at least a first section of the signal segment;

d) determining a total number of the first blocks;

e) determining a measure for a signal swing in each of the first blocks;

f) determining a number of first blocks in which the measure for the signal swing is less than a predeterminable first threshold value;

g) calculating a first quotient from the number of first blocks in which the measure for the signal swing is less than the first threshold value, and the total number of the first blocks;

h) comparing the first quotient with a second threshold value;

i) classifying a cardiac state of the human or animal organism into a first class if the first quotient is greater than the second threshold value, or classifying a cardiac state of the human or animal organism into a second class if the first quotient is not greater than the second threshold value, wherein one of the first and second classes is indicative of a physiological state of the organism and the other of the first and second classes is indicative of a pathophysiological state of the organism;

j) initiating or preventing a stimulation of a cardiac region of the heart of the human or animal organism by means of a stimulation unit depending on the classification that has taken place.

12. A method for signal processing, having the following steps:

a) detecting a cardiac signal from a human or animal organism in a time-dependent manner by means of a detection unit of an implantable medical device for detecting a cardiac signal from a human or animal organism and for stimulating the human or animal heart;

b) defining a signal segment which extends over an adjustable first temporal length of the cardiac signal;

c) subdividing the signal segment into first blocks in at least a first section of the signal segment;

d) determining a total number of the first blocks;

e) determining a measure for a signal swing in each of the first blocks;

f) determining a number of first blocks in which the measure for the signal swing is less than a predeterminable first threshold value;

g) calculating a first quotient from the number of first blocks in which the measure for the signal swing is less than the first threshold value, and the total number of the first blocks;

h) comparing the first quotient with a second threshold value;

i) classifying a cardiac state of the human or animal organism based on the comparing:

j) initiating or preventing a stimulation of a cardiac region of the heart of the human or animal organism by means of a stimulation unit depending on the classification that has taken place.

\* \* \* \* \*